United States Patent
Stern

(10) Patent No.: US 9,918,958 B2
(45) Date of Patent: Mar. 20, 2018

(54) TREATMENT FOR HYPOXIA

(76) Inventor: Warren Stern, Plymouth, MA (US)

(*) Notice: Subject to any disclaimer, the term of this patent is extended or adjusted under 35 U.S.C. 154(b) by 0 days.

(21) Appl. No.: 13/547,462

(22) Filed: Jul. 12, 2012

(65) Prior Publication Data

US 2013/0018092 A1 Jan. 17, 2013

Related U.S. Application Data

(60) Provisional application No. 61/508,260, filed on Jul. 15, 2011.

(51) Int. Cl.
*A61K 31/341* (2006.01)
*A61P 11/00* (2006.01)

(52) U.S. Cl.
CPC .................. *A61K 31/341* (2013.01)

(58) Field of Classification Search
CPC .................................................... A61K 31/341
See application file for complete search history.

(56) References Cited

U.S. PATENT DOCUMENTS 7,160,910 B2 * 1/2007 Safo ............ A61K 31/34
514/365

OTHER PUBLICATIONS

Li et al. in Cell Stress and Chaperones (2011) 16:267-273.*
Puente-Maestu et al. in European Respiratory Journal (2009) 33:1045-1052.*
Celli et al. in European Respiratory Journal (2004) 23:932-946.*
Abdulmalik et al. in British Journal of Haematology, 128, 552-561 (2005).*
Goodman & Gilman's The Pharmacological Basis of Therapeutics (Tenth Edition (2001), McGraw Hill, Chapter I, pp. 3-29.*
Erbland et al. in Chest 1990;97:1289-1294.*
Eaton et al. in European Respiratory Journal (2002) 20:306-312.*
Peinado et al. in The American Journal of Physiology 274 (Lung Cell. Mol. Physiol. 18): L908-L913 (1998).*
Sumpio et al. "Cells in focus: endothelial cell" in Int J Biochem Cell Biol. Dec. 2002;34(12):1508-12. (Abstract).*
Reagan-Shaw et al. in FASEB Journal 22, 659-661 (2007).*

* cited by examiner

*Primary Examiner* — Dennis Heyer
(74) *Attorney, Agent, or Firm* — Verrill Dana, LLP; Wayne A. Keown

(57) ABSTRACT

The invention provides a method for treating hypoxia in a normal subject, comprising administering 5-HMF to the subject.

6 Claims, 2 Drawing Sheets

Note -- Pre-dose SpO$_2$ changes at the end of the hypoxia test periods were: placebo -11.5%, 300 mg -10.8%, 1000 mg -11.7% 2000 mg -9.8%, and 4000 mg -10.2%

TREATMENT FOR HYPOXIA

BACKGROUND OF THE INVENTION

Hypoxia is the absence or shortage of oxygen in tissues. Hypoxia leads to tissue morbidity and even death. Humans have evolved a hypoxia adaptive response, to reductions in the $O_2$ transport capacity of blood caused by blood loss or anemia. The reduced $O_2$ transport capacity of blood in these situations can be partially compensated by a decrease in Hb-$O_2$ affinity, which under normoxia increases $O_2$ unloading to tissue without reducing $O_2$ uptake in the lungs. The decreased Hb-$O_2$ affinity is mediated by an increase in the red-cell 2,3-diphosphoglycerate concentration (DPG), a decrease in the pH of blood (Bohr Effect), and an increase in $CO_2$ (Haldane Effect). This response is appropriate for blood loss or anemia, but is maladaptive for hypoxia caused by other clinical conditions.

Clinically, hypoxic conditions result from apneas, sleep apneas, impaired respiration, high altitude, hemoglobin mutations, blood loss, anemia and inadequate delivery of oxygen by a therapeutic oxygenation device. Other conditions that cause impaired respiration include respiratory diseases, pulmonary infections, asthma, pneumonia, interstitial lung disease, heart attack, stroke, congestive heart failure, unstable angina, drowning, multiple organ failure, reperfusion injury, pulmonary hypertension, pulmonary embolism, brain embolism, peripheral artery disease, deep vein thrombosis that leads to a clot in the lung, trauma, chronic obstructive pulmonary disease, sickle cell disease, chronic breathlessness, chronic obstructive pulmonary disease, bronchiectasis, valvular heart disease, left and/or right ventricular failure, motor neurone disease, obesity, anxiety, end-stage cancer and lung cancer. The primary treatment for hypoxia is the use of a therapeutic oxygenation device to deliver higher levels of oxygen in the inspired air or the use of a drug or medical device that directly reverses the cause of the impaired respiration, such as an antibiotic to treat pneumonia or a bronchodilator for the treatment of asthma.

5-hydroxymethyl-2-furfural (5-HMF) is being developed as a therapeutic treatment for sickle cell disease (SCD). U.S. Pat. No. 7,160,910 discloses therapeutic efficacy of 5-HMF in a murine model for SCD. Human clinical trials are being conducted under the auspices of the National Institutes for Health.

Abdulmalik et al., Br. J. Hematol. 128: 552-561 (2004) teaches that 5-HMF provides in vivo protection against the lethal effects of hypoxia in a sickle cell disease mouse model, and that this is the result of a lower P50 (left shift) in the SCD Hb, thus reducing the formation of sickled red blood cells in conditions of insufficient oxygen delivery from the inspired air. Thus, according to Abdumalik, the beneficial effect of 5-HMF in prolonging survival in the hypoxic state is due to the inhibition of RBC sickling, a phenomenon that is unique to SCD and would not be found in normal subjects.

Li et al., Cell Stress and Chaperones (published on-line Apr. 15, 2011) discloses a mouse model simulation of altitudinal hypoxia (hypobaric hypoxia) using a decompression chamber to simulate an altitude of 9,500 meters. 5-HMF was reported to increase survival of mice under these conditions. The authors attributed this to a partial blocking by 5-HMF of altitude-induced increases in permeability of blood brain barrier, thus protecting the brain from swelling and injury. According to this explanation, 5-HMF would be expected to be effective for treating only altitudinal hypoxia, and not other hypoxias that act other than by increasing the permeability zing of the blood brain barrier.

There is, therefore, a need for additional treatments for normal subjects who have hypoxia, other than altitudinal hypoxia.

BRIEF SUMMARY OF THE INVENTION

The invention relates to the treatment of hypoxia. The inventor has surprisingly discovered that 5-hydroxymethyl-2-furfural (5-HMF) can be used for the treatment of normal subjects having hypoxia, other than altitudinal hypoxia.

The invention provides a method for treating hypoxia in a normal subject comprising administering to the subject an effective amount of 5-HMF, wherein the hypoxia is not altitudinal hypoxia. In the methods according to the invention, 5-HMF may be administered alone, or in combination with a medication that treats the underlying cause of the hypoxia.

DETAILED DESCRIPTION OF THE PREFERRED EMBODIMENTS

Figure 1:
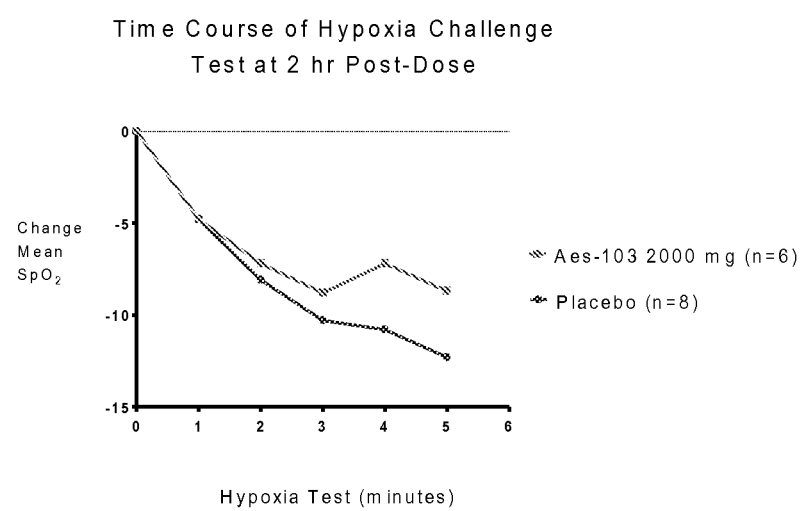
FIG. 1 illustrates the effect of 5-HMF during a hypoxic challenge.

The invention relates to the therapeutic treatment of hypoxia in normal subjects. The invention provides methods for treating hypoxia in a normal subject comprising administering to the subject an effective amount of 5-HMF, wherein the hypoxia is not altitudinal hypoxia. The therapeutic effect of 5-HMF is attributed to the induction of an increase in affinity for oxygen in normal hemoglobin. In the methods according to the invention, 5-HMF may be administered alone, or in combination with a medication that treats the underlying cause of the hypoxia.

In a first aspect, the invention provides a method for treating a normal subject having hypoxia comprising administering to the subject an amount of 5-HMF that is effective at reducing signs and symptoms of hypoxia in the subject, wherein the hypoxia is not altitudinal hypoxia. Treatment of altitudinal hypoxia has been described in U.S. Patent Publication No. 2012/0041060.

In some embodiments, the hypoxia is caused by a disease or condition selected from the group consisting of respiratory diseases, pulmonary infections, asthma, pneumonia, interstitial lung disease, heart attack, stroke, congestive heart failure, unstable angina, drowning, multiple organ failure, reperfusion injury, pulmonary hypertension, pulmonary embolism, brain embolism, peripheral artery disease, deep vein thrombosis, trauma, chronic obstructive pulmonary disease, sleep apneas, impaired respiration due to drugs or drug overdoses, mechanical asphyxiation, chronic breathlessness, chronic obstructive pulmonary disease, bronchiectasis, valvular heart disease, left and/or right ventricular failure, motor neurone disease, obesity, anxiety, end-stage cancer, other terminal illness, lung cancer and other factors that reduce the capacity of the lung to receive or absorb oxygen or which reduce the ability of the brain to properly regulate inhalation/exhalation or due to restriction of blood flow to organs, resulting in hypoxic regions within the body.

The subject is administered an amount of 5-HMF that is effective at reducing signs and symptoms of hypoxia. In preferred embodiments, the method according to this aspect of the invention comprises administering to the subject an amount of 5-HMF that is sufficient to reduce signs and symptoms of hypoxia, but low enough to minimize unwanted side effects. In some embodiments the subject is administered from about 300 mg to about 10,000 mg 5-HMF. In some embodiments the subject is administered from about 500 mg to about 4,000 mg 5-HMF. In some embodiments the subject is administered from about 500 mg to about 3,000 mg 5-HMF. In some embodiments the subject is administered from about 500 mg to about 1,000 mg 5-HMF. In some embodiments the subject is administered from about 500 mg to about 2,000 mg 5-HMF. In some embodiments the subject is administered from about 1,000 mg to about 2,000 mg 5-HMF. In some embodiments the subject is administered from about 3,000 mg to about 10,000 mg 5-HMF.

The methods according to the invention are effective at reducing one or more signs or symptoms of hypoxia. Among the one or more clinical signs or symptoms of hypoxia to be reduced are tissue damage, mental confusion, impaired motor responses, physical tiredness, loss of conscious and brain and/or lung edema.

In some embodiments, the 5-HMF is administered in a pharmaceutical formulation. Such pharmaceutical formulations further comprise a pharmaceutically acceptable diluent, carrier, or excipient. Such formulations are well known in the art and are described, e.g., in Remington's Pharmaceutical Sciences, 18th Edition, ed. A. Gennaro, Mack Publishing Co., Easton, Pa., 1990. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the compounds described above, diluents, fillers, salts, buffers, stabilizers, solubilizers, and other materials well known in the art.

As used herein, the term pharmaceutically acceptable salts refers to salts that retain the desired biological activity of the above-identified compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

In a second aspect, the method according to the invention comprises administering to a normal subject 5-HMF in combination with one or more medication that treats the underlying condition that causes the hypoxia.

As non-limiting examples, if the subject has hypoxia caused by pneumonia, 5-HMF can be administered in combination with an antibiotic, an anti-viral drug, an antifungal drug, or an anti-protozoal drug. If the subject has cancer, 5-HMF can be administered in combination with an anti-cancer chemotherapeutic drug or an anti-cancer monoclonal antibody. If the subject has had a stroke, 5-HMF can be administered in combination with an antithrombotic agent, such as tissue plasminogen activator (t-PA) or streptokinase, in combination with an anti-platelet drug, such as aspirin, a thienopyridine, clopidogrel, or a glycoprotein IIb/IIIa inhibitor, or in combination with a blood thinner such as heparin or hirulog, or any combination of these agents. If the subject has peripheral artery disease, the 5-HMF can be administered in combination with a cholesterol lowering drug, such as a statin, in combination with an anti-platelet drug, in combination with a symptom relief medication, such as cilostazol or pentoxifylline, or any combination of these agents. If the subject has congestive heart failure, 5-HMF can be administered in combination with an angiotensin converting enzyme (ACE) inhibitor, such as captopril, enalapril, lisinopril, benazepril, or ramipril, in combination with an angiotensin receptor blocker, such as losartan, candesartan, telmisartan, valsartan, irbesartan or olmesartan, in combination with a beta blocker, such as carvedilol or metoprolil, in combination with digoxin or a diuretic, or any combination of these agents. If the subject has reperfusion injury, 5-HMF can be administered in combination with a calcium channel antagonist, an anti-CD18 antibody, hydrogen sulfide, or any combination of these agents.

For purposes of the invention, the term "normal subject" means a subject who does not have sickle cell diseasae. The term "having hypoxia" means that the subject has one or more tissues that has reduced oxygen sufficient to cause damage to, or loss of function of, the one or more tissues. The term "subject" refers to a human patient. The term "in combination with" means in the course of treating the same disease in the same subject, and includes administering 5-HMF and a medication that treats the underlying cause of hypoxia (and optionally an agent that extends the half-life of 5-HMF in the body of the subject) in any order, including simultaneous administration, as well as any temporally spaced order, for example, from sequentially with one immediately following the other to up to several hours apart. The administration of 5-HMF and other medications or agents may be by the same or different routes. Preferred routes include parenteral, intranasal and especially oral.

Example 1

Safety of 5-HMF

The study was a double-blind, placebo (n=8) controlled single ascending dose (SAD) trial examining 5-HMF doses of 300 mg, 1000 mg, 2000 mg and 4000 mg (n=6 per dose). Overall 5-HMF was shown to be safe and well tolerated. Moreover IND-enabling repeat dose animal toxicology and safety data suggest a wide safety window in humans is likely.

Example 2

Increase in Blood Oxygenation Under Hypoxic Challenge

The hypoxic challenge test was conducted it the following manner: using face masks and air tanks containing 12% oxygen (compared to 21% oxygen in normal air at sea level), subjects inhaled the 12% hypoxic mixture for 5 minutes at a time just prior to starting the dose of study medication (5-HMF or placebo, double-blind) and then again at each of the time intervals 0.75, 2, 4 and 8 hours after the dose. A finger tip oxygen sensing probe connected to a pulse oximeter provided continuous measurement of SpO2 values (percentage of hemoglobin containing at least one oxygen molecule) and the SpO2 values were recorded every 20 seconds during the hypoxic challenge and during a 3-minute recovery period (during which normal air was inspired). The hypoxia challenge was aborted if SpO2 values fell to less than 85%. FIG. 1 illustrates the effect of 5-HMF during a hypoxic challenge. The data compares the fall in mean SpO2 values of placebo and the 2000 mg dose of 5-HMF prior to a hypoxic challenge given at the 2 hour time point post-dose. The mean change in SpO2 levels from start is shown for each one-minute interval of the 5-minute hypoxic challenge. The increase in blood oxygenation from 5-HMF (shown by a less severe decrease in SpO2 during the hypoxic challenge) begins to become apparent after one minute of inhalation of hypoxic air when the SpO2 levels of both placebo and drug subjects fall by 5 units and the 5-HMF induced improvement, relative to placebo, in SpO2 is thereafter present for the remainder of the challenge period. It is noteworthy that the difference between placebo and drug becomes greater as the level of hypoxia in the placebo subjects increases. In vivo studies in animal models also suggest the impact of 5-HMF is greater when the level of hypoxia increases. Since the level of hypoxic challenge in this initial human study was moderate (no clinical symptoms of hypoxia were present), the impact of 5-HMF should be even greater when the hypoxic challenge is more extreme.

Example 3

Dose-dependence of 5-HMF in Blood Oxygenation

Figure 2:
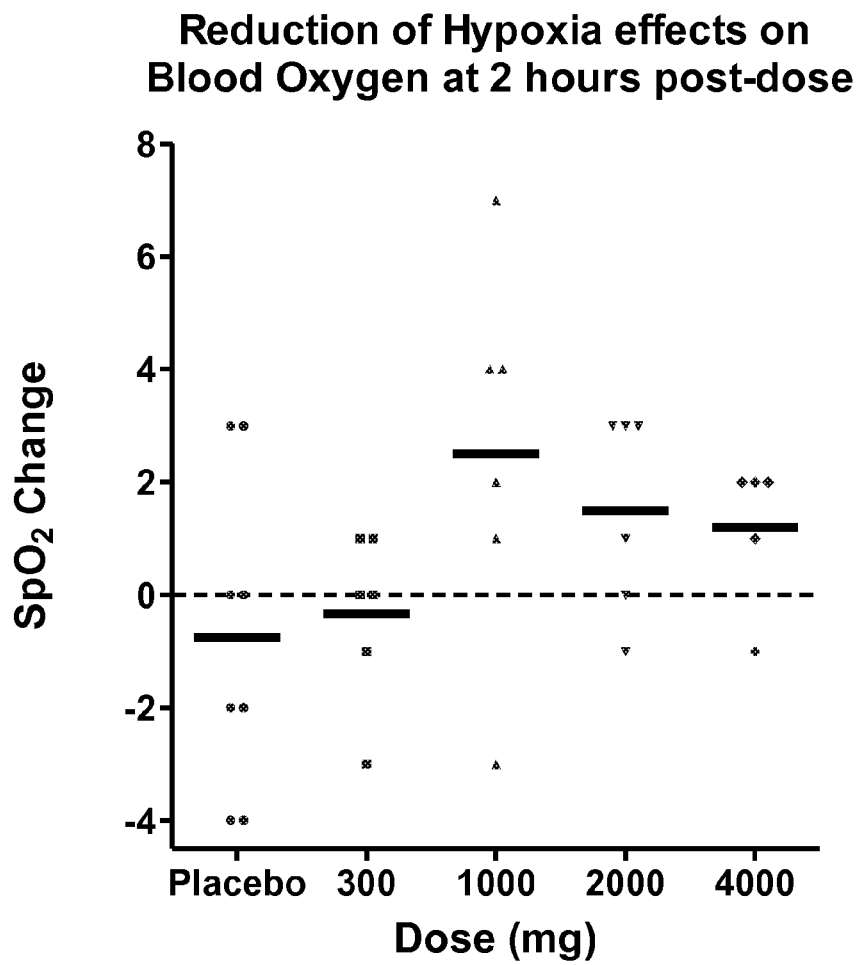
FIG. 2 shows the dose-dependency of the effect of 5-HMF during a hypoxic challenge.

An illustration of the dose-dependent ability of 5-HMF to impact blood oxygenation during a hypoxic challenge is shown in FIG. 2. Because there are appreciable inter-individual differences in the magnitude of the decline of SpO2 in response to a hypoxic challenge, each subject (both placebo and 5-HMF) was tested for the decline in SpO2 at the 5 minute time point for both (i) the challenge given prior to the dose of placebo or 5-HMF and (ii) the challenge given 2 hours after the dose of placebo or 5-HMF. The dotted line in FIG. 2 represents the "baseline" amount of decline occurring during the challenge given prior to dosing placebo or 5-HMF. The results of the decline in SpO2 for each subject at the end the challenge given 2 hours post-dose results were compared to the subject's baseline amount. Thus each subject acted as his/her own control. The blue dots represent individual subject scores and the horizontal black line is the mean SpO2 change relative to the pre-dose hypoxic challenge. Thus, as shown for the 1000 mg dose of 5-HMF, this dose resulted in an approximately 2.5 unit increase in ending SpO2 levels at 2 hours post-dose relative to the decline seen in the same subjects when tested prior to the dose. In contrast, subjects receiving placebo, had a further decline of about −0.75 units relative to their baseline response to hypoxia prior to receiving placebo. As shown in FIG. 2, results indicate that during a hypoxia challenge, 5-HMF increased the blood oxygen saturation of the test subjects compared to placebo at all dose levels, but the effect at 300 mg was small and 1000-4000 mg is probably the optimal dose. The difference from placebo of the most active dose levels (top three doses) was statistically significant ($p=0.0498$).

Example 4

Treatment of Moderate and Severe Hypoxia

Effects of 500, 1000, 2000, 4000 mg of 5-HMF and placebo on cognitive functioning and exercise capacity effects are measured for both moderate (SpO2 75-85%) and severe (SpO2 60-70%) hypoxia in 15 normal volunteers per hypoxia level. This is a double-blind crossover study in which efficacy endpoints are measured prior to the onset of hypoxia, 1-2 hours after the onset of hypoxia, after which study drug is administered and measurements are taken 1.5-2 hours and 3.5-4 hours post-dose. Using the best dose level from this, part of the study a subsequent 3-day moderate and a 3-day severe hypoxia exposure period is evaluated in parallel sets of subjects who receive multiple daily doses of 5-HMF or placebo. Cognitive and exercise capacity tests are administered prior to the onset of hypoxia and at 1-2 hours and 3-4 hours after the third dose of study drug on Days 1 and 2 (steady state being achieved by Day 2) and 3. On Day 3, all subjects receive study drug on the morning dose and placebo on subsequent doses in order to determine the rate of offset of drug related improvements. Secondary objectives include measurement of the safety of 5-HMF in non-hypoxic and hypoxic conditions, as reflected by adverse events, vital signs (heart rate, blood pressure, respiratory rate), clinical chemistry and hematological function. Pharmacodynamic measures include changes in SpO2 values and p50 values.

All references cited herein reflect the level of knowledge in the art and are hereby incorporated by reference in their entirety. Any conflict between the teachings of the cited references and this specification will be resolved in favor of the latter.

Those skilled in the art will recognize that the invention includes equivalents of the formulations and methods described herein.

What is claimed is:

1. A method for treating chronic obstructive pulmonary disease in a normal human subject, comprising administering to the subject from about 500 mg to about 2,000 mg 5-hydroxymethyl-2-furfural (5-HMF).

2. The method according to claim 1, wherein the subject is administered from about 1,000 mg to about 2,000 mg 5-HMF.

3. The method according to claim 1, wherein the subject is administered from about 500 mg to about 1,000 mg 5-HMF.

4. A method for treating hypoxia caused by COPD in a normal human subject, comprising administering to the subject from about 500 mg to about 2,000 mg 5-hydroxymethyl-2-furfural (5-HMF) in combination with a drug to treat the COPD.

5. The method according to claim 4, wherein the subject is administered from about 500 mg to about 1,000 mg 5-HMF.

6. The method according to claim 4, wherein the subject is administered from about 1,000 mg to about 2,000 mg 5-HMF.

* * * * *